United States Patent [19]

Halpin et al.

[11] Patent Number: 5,846,767
[45] Date of Patent: Dec. 8, 1998

[54] EXPRESSION OF SELF PROCESSING POLYPROTEINS IN TRANSGENIC PLANTS

[75] Inventors: Claire Halpin; Martin Denis Ryan, both of St. Fort, United Kingdom

[73] Assignee: Zeneca Limited, London, England

[21] Appl. No.: 646,293

[22] PCT Filed: Dec. 19, 1994

[86] PCT No.: PCT/GB94/02765

§ 371 Date: May 10, 1996

§ 102(e) Date: May 10, 1996

[87] PCT Pub. No.: WO95/17514

PCT Pub. Date: Jun. 29, 1995

[30] Foreign Application Priority Data

Dec. 23, 1993 [GB] United Kingdom .................... 9326271

[51] Int. Cl.$^6$ ........................... C12P 21/06; C12N 15/42; C12N 15/63; C12N 15/82; C07H 21/04
[52] U.S. Cl. .................. 435/69.1; 435/172.3; 435/320.1; 435/419; 536/23-72; 800/205
[58] Field of Search ................................ 435/69.1, 172.3, 435/320.1, 419; 536/23-72; 800/205

[56] References Cited

U.S. PATENT DOCUMENTS 5,162,601 11/1992 Slightom ................................ 800/205

OTHER PUBLICATIONS

Palmenberg. Proteolytic processing of picornaviral polyprotein. Annual Review of Microbiology. 44:603–623, 1990.
Carrington et al. Expression of potyviral polyproteins in transgenic plants reveals three proteolytic activities required for complete processing. The EMBO Journal. 9(5):1347–1353, 1990.
Nucleotide sequence and genome organization of foot–and–mouth disease virus. Nucleic Acids Research. 12(16):6587–6600,1984.
The complete nucleotide sequence of the RNA coding for the primary translation product of foot and mouth disease virus. 12(5):2461–2472, 1984.
The 5' untranslated region of PVY RNA, even located in an internal position, enables enitiation of translation. 7(4):367–379, 1993.
Ryan et al: "Cleavage of foot–and–mouth disease virus polyprotein is mediated by residues located within a 19 amino acid sequence", J. Gen. Virol., vol. 72, 1991, pp. 2727–2732.
Roosien et al: "Synthesis of foot–and–mouth disease virus capsid proteins in insect cells using baculovirus expression vectors", J. Gen. Virol., vol. 71, 1990, pp. 1703–1711.
Ryan et al: "Foot–and–mouth disease virus 2A oligopeptide mediated cleavage of an artificial polyprotein", The EMBO J., vol. 13, 1994, pp. 928–933.

*Primary Examiner*—David T. Fox
*Assistant Examiner*—Thanda Wai
*Attorney, Agent, or Firm*—Marian T. Thomson

[57] ABSTRACT

A method for the expression of multiple proteins in a transgenic plant comprising inserting into the genome of the plant a gene construct comprising a 5'-region which includes a promoter which is capable of initiating transcription of a structural gene under the control thereof, a protein encoding sequence coding for more than one protein and a 3'-terminator region which includes a polyadenylation signal, each of the protein encoding sequences being separated from an adjacent protein encoding sequence by a DNA sequence which on translation provides a cleavage site whereby the expressed polyprotein is post-translationally processed into the component protein molecules. The DNA sequence which encodes the post-translation cleavage site may be derived from a virus, particularly a picornavirus. In a preferred embodiment the DNA sequence providing the cleavage site encodes the amino acid sequence NFDLLKLAGDVESNPGPFF.

17 Claims, 4 Drawing Sheets

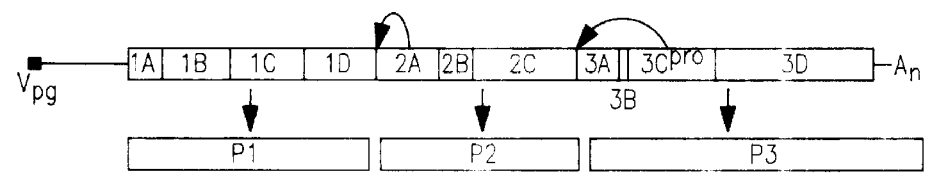
FIG. 1A
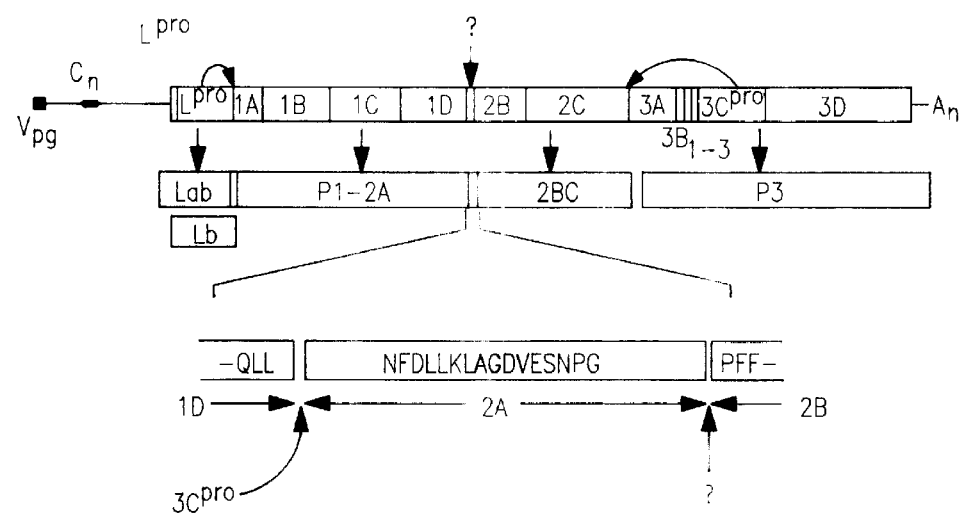
FIG. 1B
FIG. 1C

EXPRESSION OF SELF PROCESSING POLYPROTEINS IN TRANSGENIC PLANTS

This application is a 371 of international application PCT/GB94/02765, filed Dec. 19, 1994.

BACKGROUND OF THE INVENTION

This invention relates generally to the expression of self-processing polyproteins in transgenic plants.

The relative levels of expression of several introduced genes in transgenic plants is notoriously influenced by "position effects" determined by the particular site of transgene integration into the genome. Even when introduced genes are linked on the same T-DNA, driven either by convergent or divergent promoters, they are usually not co-ordinately expressed at similar levels. This poses particular problems when high levels of expression of a number of introduced activities is required, for instance when attempting to express novel biochemical pathways in plants. In an attempt to achieve tissue specific, coordinated expression of two proteins, other researchers have linked genes by co-transference on the same T-DNA. The expression levels of linked nopaline synthase (nos) and octopine synthase (ocs) genes and closely adjacent neomycin phosphotransferase II (NPTII) and chloramphenicol acetyl transferase (CAT) reporter genes were found to vary independently. Another strategy was to link genes via adjacent and divergent promoters. Whereas coordinated expression of the Cab22L and Cab22R genes of petunia was achieved, a similar approach using the CAT and GUS genes produced a high degree of variation of CAT and GUS activities within individual transgenes.

Linking proteins in the form of polyproteins is a strategy adopted in the replication of many viruses. On translation, virus-encoded proteinases mediate extremely rapid intramolecular (cis) cleavages of the polyprotein to yield discrete protein products.

A number of viral proteinases have been partially characterised and are thought to be related, both structurally and in catalytic mechanism, to cellular proteinases. In the picornaviridae a single long open reading frame encodes a polyprotein of some 225kD, but full-length translation products are not normally observed due to extremely rapid "primary" intramolecular (cis) cleavages mediated by virus encoded proteinases. In the case of the entero- and rhinoviruses, a primary cleavage occurs between the P1 capsid protein precursor and the replicative domains of the polyprotein (P2, P3; FIG. 1A). This cleavage is mediated by a virus encoded proteinase ($2A^{pro}$), of some 17kDa, cleaving at its own N-terminus.

The aphtho-, or Foot-and-Mouth Disease (FMD), viruses form a distinct group within the picornaviridae. FMDV polyprotein undergoes a primary polyprotein cleavage at the C-terminus of the 2A region between the capsid protein precursor (P1-2A) and replicative domains of the polyprotein 2BC and P3 (FIG. 1B). Precursors spanning the 2A/2B cleavage site are not detected during native polyprotein processing. This situation is somewhat analogous to the 2A cleavage in entero- and rhinoviruses described above. However the 2A region of the FMDV polyprotein was demonstrated to be only 16 amino acids long (FIG. 1,C). The predicted amino acid sequence of this region, is totally conserved amongst all aphthovirus genomic RNAs sequenced to date. The FMDV 2A region also shows high similarity to the C-terminal region of the approximately ten fold larger 2A protein of another genus of the picornaviridae, the cardioviruses.

SUMMARY OF THE INVENTION

According to the present invention, there is provided a method for the expression of multiple proteins in a transgenic plant comprising inserting into the genome of the plant a gene construct comprising a 5'-region which includes a promoter which is capable of initiating transcription of a structural gene under the control thereof, a protein encoding sequence coding for more than one protein and a 3'-terminator region which includes a polyadenylation signal, each of the said protein encoding sequences being separated from an adjacent protein encoding sequence by a DNA sequence which on translation provides a cleavage site whereby the expressed polyprotein is post-translationally processed into the component protein molecules.

Preferably the DNA sequence which encodes the post-translation cleavage site is derived from a virus, particularly a picornavirus.

Preferably also the DNA sequence providing the cleavage site encodes the amino acid sequence NFDLLKLAGD-VESNPGPFF [SEQ ID NO.1]. However, it is well known that variations may be made in amino acid sequences which do not greatly affect function and it is intended that such variants of the said sequence and the nucleotide which encodes it are within the scope of this invention.

Thus multiple genes are inserted into a plant genome under the control of a single promoter, in the form of a self-processing polyprotein.

We have found that FMDV 2A represents a polyprotein region whose sole function in the viral genome is to effect or direct a single cleavage at its own C-terminus, functioning only in cis. Due to its small size, FMDV 2A (and related sequences or derivatives) presents an ideal candidate for engineering into plant polyprotein expression vectors.

The inclusion of such proteinase or cleavage sequences in plant transformation constructs enables the expression from a single promoter of multiple introduced proteins, initially linked as a polyprotein, in plant cells and plants.

Initial characterisation of the FMDV 2A region, using a series of recombinant FMDV polyproteins, showed that the FMDV 2A/2B cleavage activity was mediated by residues located within the 19 amino acid sequence NFDLLKLAGD-VESNPGPFF [SEQ ID NO.1] spanning the FMDV 2A region (Ryan et al, 1991). It was found that FMDV 2A does not act as a substrate for a proteinase located elsewhere within the FMDV polyprotein or absolutely require particular FMDV domains for activity. Three explanations may account for a co-translational cleavage associated with such a short sequence; (i) FMDV 2A functions as a substrate for a cellular proteinase, which, to account for the observed cleavage kinetics, would need to be closely coupled to translation, (ii) the FMDV 2A sequence in some manner disrupts the normal peptide bond formation during translation, or (iii) the FMD 2A sequence possesses an entirely novel type of proteolytic activity. These data do not, however, clarify to what extent the 2A region could function independently of the physical environment provided by FMDV polyprotein sequences. To address this question we have studied proteolysis associated with FMDV 2A in a completely foreign context, that of a synthetic polyprotein designed such that two reporter genes flank sequences from the FMDV 2A region of the polyprotein.

We have constructed a plasmid (pCAT2AGUS) in which the 20 amino acid sequence spanning FMDV 2A was inserted between the reporter genes chloramphenicol acetyl transferase (CAT) and β-glucuronidase (GUS) maintaining a single, long, open reading frame (FIG. 2). Translation studies were performed in three systems; (i) a coupled transcription/translation (TnT) rabbit reticulocyte system, (ii) a wheat germ lysate and (iii) a human cell line (HTK-143) infected with the recombinant vaccinia virus vTF7-3 expressing T7 RNA polymerase.

Translation directed by pCAT2AGUS showed three major translation products in all translation systems. The uppermost band corresponded to the expected [CAT2AGUS] polyprotein translation product and was immunoprecipitated by anti-CAT and anti-GUS antibodies. The second band co-migrated with GUS and was immunoprecipitated only by antibodies directed against GUS and corresponded to a GUS cleavage product. The lower band migrated somewhat more slowly than CAT and was immunoprecipitated by anti-CAT and anti-2A antibodies but not anti-GUS antibodies and corresponded to the [CAT2A] cleavage product. Densitometric analysis determined that 80% of the translated polyprotein had undergone cleavage to [CAT2A] and [GUS]. Assays provided evidence that both cleaved proteins were enzymically active.

These analyses show that the inserted FMDV sequence can function in a manner similar to that observed in FMDV polyprotein processing: the [CAT2AGUS] polyprotein undergoes a co-translational, apparently autoproteolytic, cleavage yielding [CAT-2A] and GUS. It is clear that the 20 amino acid FMDV 2A-spanning sequence does not require other domains within the FMDV polyprotein to function and is an autonomous element capable of mediating cleavage—even in a completely foreign context. Our analysis of N-terminally truncated forms of FMDV 2A show that the 13 residue oligopeptide (-LKLAGDVESNPGP- [SEQ ID NO.2]) is able to mediate cleavage whereas the 11 residue oligopeptide (-LAGDVESNPGP-[SEQ ID NO.3]) is not. However the final proline residue, which comes after the actual 2A cleavage site and constitutes the amino-terminal residue of 2B in FMDV, is necessary for cleavage. In addition we have evidence that an oligopeptide comprising the C-terminal 14 residues of the EMC 2A protein together with the N-terminal proline residue of EMC protein 2B can also mediate cleavage in a foreign context, although to a lower level than FMD 2A We are currently determining by mutagenesis the exact amino acid sequences which permit cleavage in an attempt to optimise the reaction.

FMDV 2A together with the N-terminal proline residue of protein 2B may represent an entirely novel type of protein cleavage activity. Although the mechanism of cleavage is not yet understood, its utility is apparent. Because of its small size the FMDV 2A sequence or derivatives of it are particularly attractive candidates for use in plant polyprotein expression constructs enabling the coordinated and stoichiometric expression of multiple proteins from a single open reading frame.

In the model [CAT2AGUS] construct described above, the 20 amino acid 2A-spanning sequence which remains attached to CAT after cleavage from GUS, is sufficiently short that CAT activity is not impaired. We have also found no impairment of activity in similar constructs where 2A is attached to the carboxy terminus of glutathione-S-transferase or T7 RNA polymerase.

We have introduced the CAT2AGUS construct into tobacco plants and will assess the efficiency of cleavage of [CAT2A] from [GUS] in this system. However, since the cleavage has been effective in all systems tested to date, including wheatgerm lysates, efficient cleavage is expected. The FMDV 2A sequence (plus the requisite carboxy-terminal proline) inserted between protein coding sequences, may allow the engineering of plant expression vectors where multiple whole proteins or protein domains can be expressed as a polyprotein and cleaved apart co-translationally with high efficiency. This may enable the rapid introduction of entire enzyme cascades into plants.

BRIEF DESCRIPTION OF THE DRAWINGS

FIG. 1(A–C) shows: Picornavirus Primary Polyprotein Cleavages. The 5' non-coding region is capped by a small protein VPg (or 3B). The single long open reading frame and polyprotein organisation is shown (boxed areas) for both entero- and rhinovirus groups (panel A) and aphthoviruses (panel B). Arrows indicate sites of primary cleavage and the virus-encoded proteinases responsible, where known. Primary cleavage products are shown below. The amino acid sequence spanning the aphthovirus 2A region of the polyprotein is shown, the 2A oligopeptide being cleaved from the capsid protein 1D by $3C^{pro}$ in an intermolecular reaction occuring at a later stage of polyprotein processing (panel C).

DETAILED DESCRIPTION OF THE INVENTION

EXAMPLE 1

Construction of CAT and GUS Expression Vectors

Figure 2:
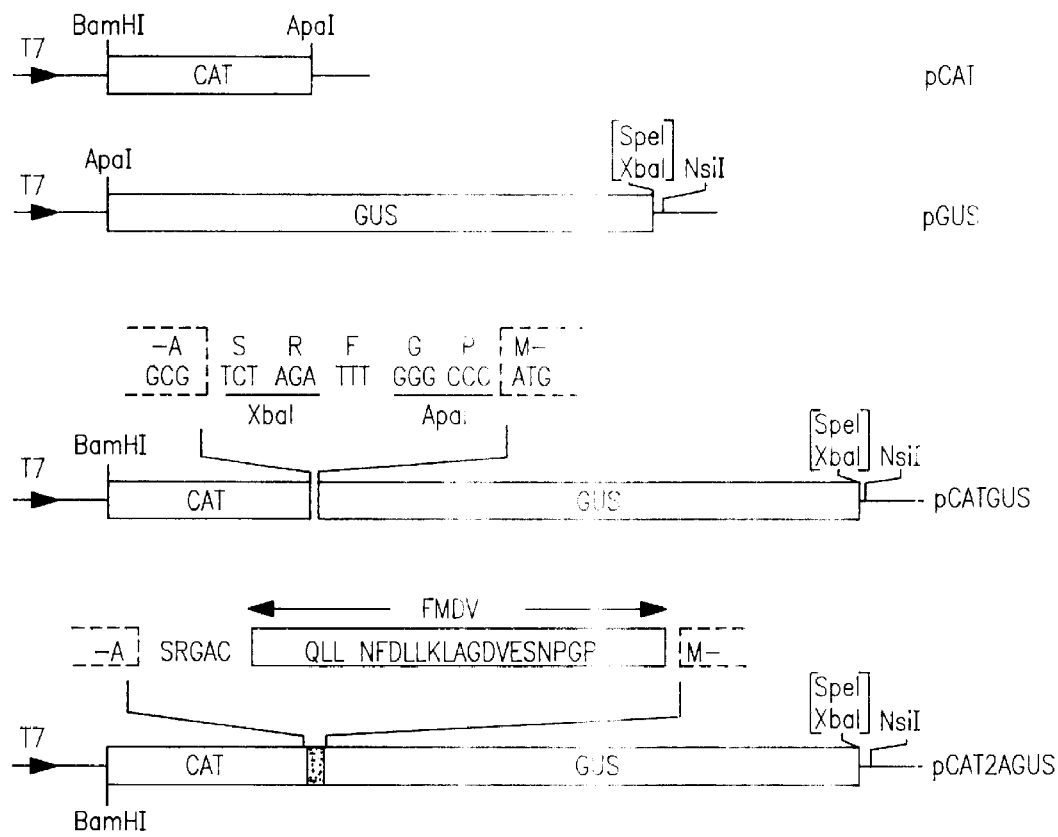
FIG. 2 shows: CAT/GUS Constructs. Boxed areas represent the single open reading frames encoding either individual proteins (CAT; pCAT20/21, GUS; pGUS12/23) or the artificial polyproteins [CATGUS] and [CAT2AGUS]. All plasmids were based on pGEM transcription vectors.

The reporter genes CAT and GUS were amplified by PCR using oligonucleotide primers such that restriction sites were created at both termini. Individual genes were cloned into pGEM transcription vectors (pCAT; pGUS) and also assembled together (pCATGUS) to produce a single open reading frame encoding the artificial polyprotein [CATGUS] (FIG. 2). Coding sequences from the FMDV 2A region were assembled in the plasmid vector pGEM 7zf(+) in such a way that a series of unique restriction sites were created throughout the sequence. The FMDV 2A sequence was excised and inserted between the CAT and GUS genes of pCATGUS to retain a single open reading frame and form construct pCAT2AGUS (FIG. 2).

EXAMPLE 2

Expression of CAT and GUS Constructs in Wheat-Germ Lysate

Figure 3:
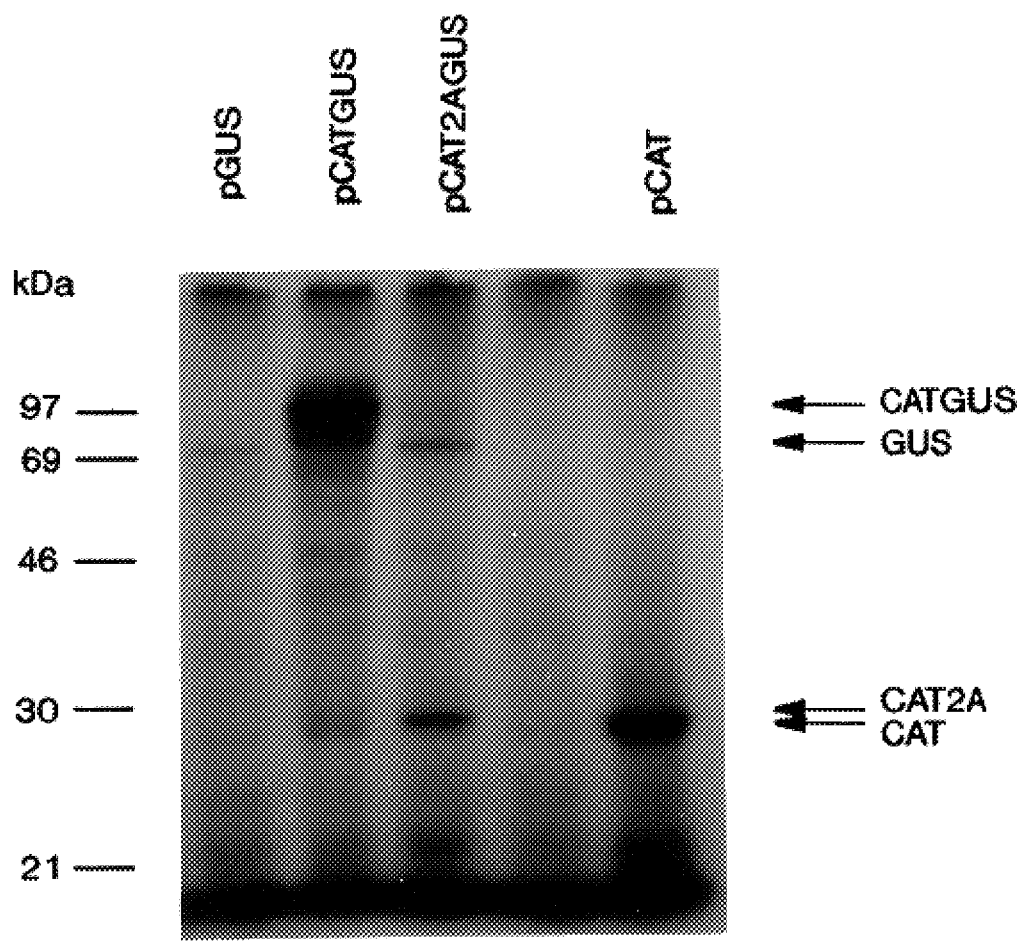
FIG. 3 shows the translation products of pGUS, pCATGUS, pCAT2AGUS and pCAT.

Translation studies were performed in a coupled transcription/translation (TnT) wheat germ system using T7 polymerase. Translation directed by plasmids pCAT, pGUS and pCATGUS yielded polypeptides of the expected molecular weight for CAT (25.7kDa), GUS (70.4kDa) and the polyprotein [CATGUS] (96.3kDa) respectively (FIG. 3, lanes 1, 4 and 2). Translation directed by pCAT2AGUS yielded two major products at 70kDa and 26kDa (lane 3). The 70kDa polypeptide migrated identically to the product of pGUS shown in lane 1 and represents GUS polypeptide processed from the [CAT2AGUS] polyprotein during translation. The 26kDa band migrated slightly more slowly than the product of pCAT shown in lane 4 and corresponds to the [CAT-2A] cleavage product. A third fainter band appeared at approx. 96kDa (lane 3) and co-migrated with the product of pCATGUS (lane 2). This corresponds to the entire polyprotein product of pCAT2AGUS and suggests that a small proportion of the polyprotein is not processed in the wheat germ lysate. Densitometric analysis of the distribution of radiolabel in the polypeptides in lane 3 showed that over 90% of the [CAT2AGUS] translation product was cleaved to [CAT-2A] and GUS.

EXAMPLE 3

Expression of [CAT2AGUS] Polyprotein in Transgenic Tobacco

Figure 4:
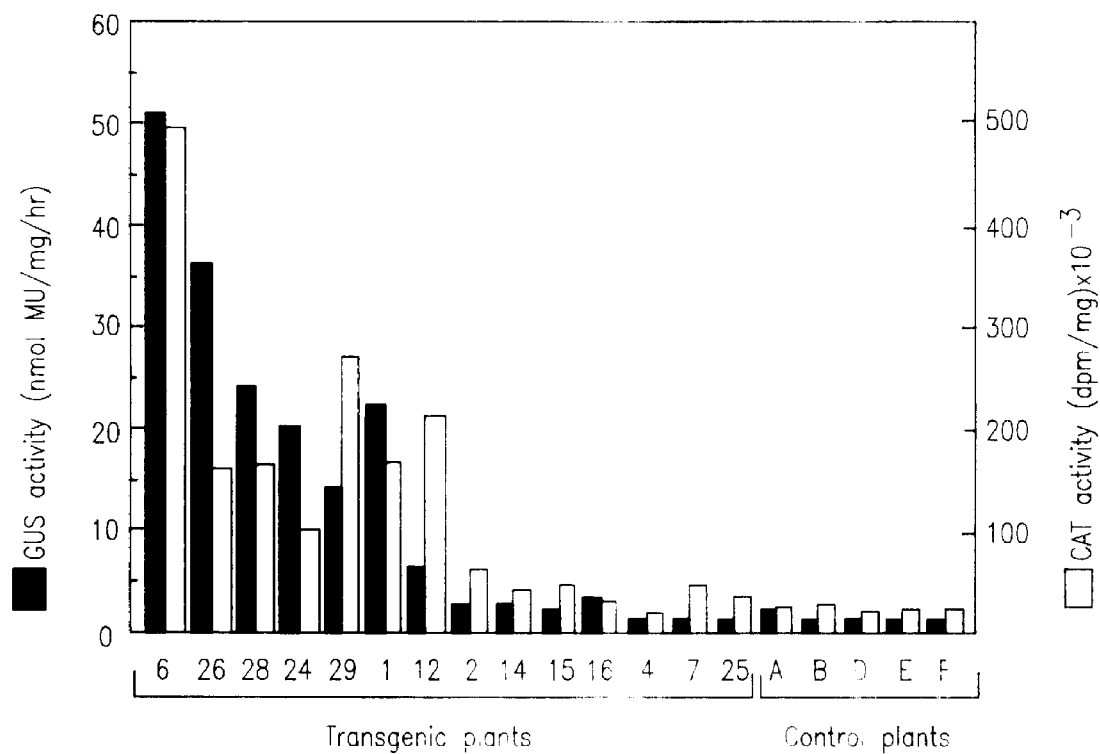
FIG. 4 shows CAT and GUS activity in transgenic plants transformed with pCAT2AGUS.

The [CAT2AGUS] portion of pCAT2AGUS was excised, inserted between the 35S CaMV promoter and nos 3' terminator and cloned into a Bin19-derived plant expression vector containing a functional neomycin phosphotransferase gene. This construct was introduced into tobacco via Agrobacterium-mediated leaf disk transformation. Transformed plants were selected and rooted on kanamycin. Protein extracts were prepared from leaves of transformed plants and assayed for GUS and CAT activities. The results are shown in FIG. 4. A high degree of correlation was found between the activities of the two enzymes in any given plant. Of 18 independent transformed plants, seven plants (6, 26, 28, 24, 29, 1 and 12) expressed both enzymes at relatively high levels. Four plants (2, 14, 15, 16) expressed both enzymes at low levels. The remaining plants (only three shown in FIG. 4, plants 4, 7 and 25) did not express either enzyme at levels above that detected in untransformed control plants (A, B, D, E, F).

Western blots of callus and leaf extracts were probed with anti-GUS antibodies. A major immuno-reactive product was detected at the expected molecular weight for GAS (70kDa) in plants transformed with [CAT2AGUS] but not in control plants. This confirmed that [CAT2AGUS] expressed in plant tissue is processed to [CAT2A] and GUS.

The data presented here demonstrates that the FMDV 2A sequence can function in a manner similar to that observed in FMDV polyprotein processing when expressed in chimeric genes in plant extracts and cells. Both in wheat germ lysates and transgenic plants, the chimeric [CAT2AGUS] polyprotein undergoes rapid, apparently autoproteolytic, cleavage to yield [CAT-2A] and GUS.

FMDV 2A may represent an entirely novel type of protein cleavage activity. Although the mechanism of cleavage is not yet understood, its utility is apparent. Because of it's small size the FMDV 2A sequence or derivatives of it are particularly attractive candidates for use in plant polyprotein expression constructs enabling the coordinated and stoichiometric expression of multiple proteins from a single open reading frame.

In the model [CAT2AGUS] construct described above, the 20 amino acid 2A-spanning sequence which remains attached to CAT after cleavage from GUS, is sufficiently short that CAT activity is not impaired. We have also shown no impairment of activity in similar constructs where 2A is attached to the carboxy terminus of glutathione-S-transferase or T7 RNA polymerase.

The FMDV 2A sequence inserted between protein coding sequences, allows the engineering of plant expression vectors where multiple whole proteins or protein domains can be expressed as a polyprotein and cleaved apart co-translationally with high efficiency. This may enable the rapid introduction of entire enzyme cascades into plants.

REFERENCES

An G. 1986 Plant Physiol. 81, 86–91.

Jones J. D. G., Gilbert D. E., Grady K. L., Jorgensen R. A. 1987 Mol.Gen.Genet. 207, p478–485.

Nagy F., Morelli G., Fraley R. T., Rogers S. G. and Chua N.-H. 1985 EMBO J. 12, 3063–3068.

Gidoni D., Bond-Nutter D., Brosio P., Jones J., Bedbrook J. and Dunsmuir P. 1988 Mol.Gen.Genet. 211, p.507–514.

Peach C. and Velten J. 1991 Plant Mol.Biol. 17, p.49–60.

Roosien, J., Belsham, G. J., Ryan, M. D., King, A. M. Q. and Vlak, J. M. (1990). J. Gen. Virol. 71, 1703–1711.

Ryan, M. D., Belsham, G. J. and King, A. M. Q. (1989). Virology 173, 35–45.

Ryan M. D., King A. M. Q. and Thomas G. P. (1991). J.Gen. Virol. 72, 2727–2732.

Ryan M. D. and Drew J. 1994 EMBO J. 13, 928–933.

We claim:

1. A gene construct for the use in the genetic modification of plants comprising in sequence, a gene promoter active in plant cells, a plurality of coding regions and a 3'-nontranslated region containing a polyadenylation signal, wherein each of the plurality of coding regions is separated by a DNA sequence which encodes an amino acid sequence comprising amino acids 5-17 of SEQ ID NO:1, and said DNA sequence does not encode an amino acid sequence which serves as a substrate for a proteinase.

2. The gene construct of claim 1, wherein the DNA sequence encodes an amino acid sequence comprising amino acids 4-17 of SEQ ID NO:1.

3. The gene construct of claim 2, wherein the DNA sequence encodes an amino acid sequence comprising amino acids 3-17 of SEQ ID NO:1.

4. The gene construct of claim 3, wherein the DNA sequence encodes an amino acid sequence comprising amino acids 2-17 of SEQ ID NO:1.

5. The gene construct of claim 4, wherein the DNA sequence encodes an amino acid sequence comprising amino acids 1-17 of SEQ ID NO:1.

6. The gene construct of claim 2, wherein the DNA sequence encodes an amino acid sequence comprising amino acids 4-18 of SEQ ID NO:1.

7. The gene construct of claim 6, wherein the DNA sequence encodes an amino acid sequence comprising amino acids 4-19 of SEQ ID NO:1.

8. The gene construct of claim 3, wherein the DNA sequence encodes an amino acid sequence comprising amino acids 3-18 of SEQ ID NO:1.

9. The gene construct of claim 8, wherein the DNA sequence encodes an amino acid sequence comprising amino acids 3-19 of SEQ ID NO:1.

10. The gene construct of claim 4, wherein the DNA sequence encodes an amino acid sequence comprising amino acids 2-18 of SEQ ID NO:1.

11. The gene construct of claim 10, wherein the DNA sequence encodes an amino acid sequence comprising amino acids 2-19 of SEQ ID NO:1.

12. The gene construct of claim 5, wherein the DNA sequence encodes an amino acid sequence comprising amino acids 1-18 of SEQ ID NO:1.

13. The gene construct of claim 12, wherein the DNA sequence encodes an amino acid sequence comprising amino acids 1-19 of SEQ ID NO:1.

14. The gene construct of claim 1, wherein the DNA sequence encodes an amino acid sequence comprising amino acids 5-18of SEQ ID NO:1.

15. The gene construct of claim 14, wherein the DNA sequence encodes an amino acid sequence comprising amino acids 5-19 of SEQ ID NO:1.

16. A method for the expression of multiple proteins in a transgenic plant, the method comprising the insertion into the genome of the plant the gene construct of claim 1.

17. A method for the expression of multiple proteins in a transgenic plant, the method comprising the insertion into the genome of the plant the gene construct of claim 13.

* * * * *

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:
( A ) LENGTH: 19 amino acids
( B ) TYPE: amino acid
( D ) TOPOLOGY: linear ( i i ) MOLECULE TYPE: protein ( x i ) SEQUENCE DESCRIPTION: SEQ ID NO:1:

```
Asn Phe Asp Leu Leu Lys Leu Ala Gly Asp Val Glu Ser Asn Pro Gly
1               5                   10                  15

Pro Phe Phe
```

( 2 ) INFORMATION FOR SEQ ID NO:2:

```
( i ) SEQUENCE CHARACTERISTICS:
        ( A ) LENGTH: 13 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

Leu  Lys  Leu  Ala  Gly  Asp  Val  Glu  Ser  Asn  Pro  Gly  Pro
  1                   5                        10
```

( 2 ) INFORMATION FOR SEQ ID NO:3:

```
( i ) SEQUENCE CHARACTERISTICS:
        ( A ) LENGTH: 11 amino acids
        ( B ) TYPE: amino acid
        ( D ) TOPOLOGY: linear ( i i ) MOLECULE TYPE: protein ( x i ) SEQUENCE DESCRIPTION: SEQ ID NO:3:

Leu  Ala  Gly  Asp  Val  Glu  Ser  Asn  Pro  Gly  Pro
  1                   5                        10
```